United States Patent [19]

Nakayama et al.

[11] Patent Number: 5,032,497

[45] Date of Patent: Jul. 16, 1991

[54] SILVER HALIDE COLOR PHOTO-SENSITIVE MATERIAL

[75] Inventors: Noritaka Nakayama; Satoshi Kawakatsu; Katsunori Katoh; Kaoru Shinozaki, all of Tokyo, Japan

[73] Assignee: Konishiroku Photo Industry Co., Ltd., Tokyo, Japan

[21] Appl. No.: 471,111

[22] Filed: Mar. 10, 1989

Related U.S. Application Data

[63] Continuation of Ser. No. 186,662, Apr. 20, 1988, abandoned, which is a continuation of Ser. No. 40,715, Apr. 21, 1987, abandoned, which is a continuation of Ser. No. 798,116, Nov. 14, 1985, abandoned.

[30] Foreign Application Priority Data

Nov. 15, 1984 [JP] Japan .................... 59-243015

[51] Int. Cl.$^5$ .................................... G03C 7/38
[52] U.S. Cl. ................................ 430/505; 430/387; 430/558
[58] Field of Search ............... 430/558 R, 387, 505

[56] References Cited

U.S. PATENT DOCUMENTS

| | | | |
|---|---|---|---|
| 2,322,027 | 6/1943 | Jelley et al. | 430/558 |
| 2,353,754 | 7/1944 | Peterson | 430/558 |
| 3,705,896 | 12/1972 | Bailey | 430/558 |
| 3,725,067 | 4/1973 | Bailey et al. | 430/558 |
| 3,758,309 | 9/1973 | Bailey et al. | 430/558 |
| 4,338,393 | 7/1982 | Bailey et al. | 430/558 |
| 4,456,681 | 6/1984 | Kadowaki et la. | 430/558 |
| 4,481,268 | 11/1984 | Bailey et al. | 430/558 |
| 4,500,630 | 2/1985 | Sato et al. | 430/558 |
| 4,510,234 | 4/1985 | Matsuzaka et al. | 430/558 |
| 4,529,691 | 7/1985 | Renner et al. | 430/558 |
| 4,540,654 | 9/1985 | Sato et al. | 430/558 |
| 4,548,899 | 10/1985 | Nakayama et al. | 430/558 |
| 4,562,146 | 12/1985 | Masuda et al. | 430/558 |
| 4,576,910 | 3/1986 | Hirano et al. | 430/558 |
| 4,581,326 | 4/1986 | Katoh et al. | 430/558 |
| 4,585,732 | 4/1986 | Kawagishi et al. | 430/558 |
| 4,590,153 | 5/1986 | Kawaqishi et al. | 430/558 |
| 4,600,688 | 7/1986 | Kawakatsu et al. | 430/558 |
| 4,607,002 | 8/1986 | Nakayama et al. | 430/558 |
| 4,623,617 | 11/1986 | Kaneko et al. | 430/558 |
| 4,639,413 | 1/1987 | Kawagishi et al. | 430/558 |
| 4,639,415 | 1/1987 | Kaneko et al. | 430/558 |
| 4,659,652 | 4/1987 | Kawagishi et al. | 430/558 |
| 4,665,015 | 5/1987 | Iijima et al. | 430/558 |
| 4,675,280 | 6/1987 | Kaneko et al. | 430/558 |
| 4,695,533 | 9/1987 | Nakayama et al. | 430/558 |
| 4,840,886 | 6/1989 | Iijima et al. | 430/558 |
| 4,882,266 | 11/1989 | Kawagishi et al. | 430/558 |

FOREIGN PATENT DOCUMENTS

| | | |
|---|---|---|
| 0073636 | 3/1983 | European Pat. Off. . |
| 073636 | 9/1983 | European Pat. Off. . |
| 143570 | 5/1985 | European Pat. Off. . |
| 177765 | 4/1986 | European Pat. Off. . |
| 178789 | 4/1986 | European Pat. Off. . |
| 1810464 | 11/1967 | Fed. Rep. of Germany . |
| 3339201 | 5/1984 | Fed. Rep. of Germany . |
| 1247493 | 9/1971 | United Kingdom . |
| 1252418 | 11/1971 | United Kingdom . |
| 1334515 | 10/1973 | United Kingdom . |
| 2135788 A | 1/1984 | United Kingdom . |
| 2132738 A | 7/1984 | United Kingdom . |
| 2132783 | 7/1984 | United Kingdom . |
| 2135788 | 9/1984 | United Kingdom . |

OTHER PUBLICATIONS

Research Disclosure 20525, May 1981.
Research Disclosure 20919, Sep. 1981.
Research Disclosure 12443, Aug. 1974.

Primary Examiner—Richard L. Schilling
Attorney, Agent, or Firm—Finnegan, Henderson, Farabow, Garrett and Dunner

[57] ABSTRACT

A silver halide photo-sensitive material having at least one silver halide emulsion layer on a support, characterized by that said silver halide emulsion layer contains at least one magenta-forming coupler of 1H-pyrazolo [3,2-c]-s-triazole type which is substituted by a tertiary alkyl group at the 3-position and, by another releasable group than a hydrogen atom at the 7-position.

10 Claims, No Drawings

SILVER HALIDE COLOR PHOTO-SENSITIVE MATERIAL

This application is a continuation of application Ser. No. 186,662, filed Spr. 20, 1988, now abandoned, which is a continuation of application Ser. No. 040,715, filed Apr. 21, 1988, now abandoned, and which is a continuation of Ser. No. 798,116, filed Nov. 14, 1985, now abandoned.

BACKGROUND OF THE INVENTION

The invention relates to a silver halide color photo-sensitive material which is highly color developable, and forms a magenta dye image improved in preservability, and especially improved in light resistance. Further detailedly, the invention relates to a silver halide color photo-sensitive material which contains a novel magenta-forming coupler of 1H-pyrazolo[3,2-C]-s-triazole type.

In general, a silver halide color photo-sensitive material exhibits a dye image by that exposed silver halide grains are reduced by a color developing agent of aromatic primary amine type, and that therewithal produced oxidation product of said color developing agent is coupled with yellow-, magenta-, and cyan-forming couplers.

While the coupler conventionally used to form said magenta dye has been of pyrazolone type, it has shortcomings of exhibiting undesirable secondary absorptions, and of being poor in preservability, and especially in formaldehyde gas resistance.

For the purpose to overcome such shortcommings as the above, various magenta-forming couplers of 1H-pyrazolo[3,2-c]-s-triazole type have been proposed so far. These couplers, which have been described in U.S. Pat. No. 3,725,067, and British Patent Nos. 1,252,418 and 1,334,515, for example, surpass magenta-forming couplers of pyrazolone type in terms of elimination of secondary absorptions, but are still insufficient in improvement of formaldehyde resistance and are little improved in light resistance of dye image. Compounds described in Research Disclosure, No. 12443 also can not be put to practical use of the art in terms of color developability at all. Magenta-forming couplers of 1H-pyrazolo [3,2-c]-s-triazole type, described in Japanese Patent O.P.I. Publication No. 2045/1983, is considerably improved in formaldehyde resistance of dye image, and in color developability, but is still little in terms of light resistance of dye image.

Couplers described in Japanese Patent O.P.I. Publication Nos. 99437/1984 and 125732/1984 also are improved in color developability, but less improved in light resistance of dye image. In case of those described in the latter Publication No. 125732/1984, the light resistance of dye image is not improved without combined use of another certain additive. Only the coupler of Compound No. 19 in the specification of the former Publication No. 99437/1984 is somewhat improved in light resistance of dye image, but still unsatisfactory.

Thus, while magenta-forming couplers of 1H-pyrazolo [3,2-c]-s-triazole type have been paid attention to because of their elimination of secondary absorptions, and high formaldehyde resistance, it should be noted that they have been little improved in terms of light resistance of dye image so far.

The object of the invention is to present a silver halide color photo-sensitive material which is not only excellent in both light resistance, and formaldehyde resistance, but also high in color developability.

The above object of the invention is attained by a silver halide color photo-sensitive material having at least one silver halide emulsion layer on a support, characterized by that said silver halide emulsion layer contains at least one magenta-forming coupler of 1H-pyrazolo[3,2-c]-s-triazole type which is substituted by a tertiary alkyl group at the 3-position, and by another releasable group than a hydrogen atom at the 7-position.

As a result of keen studies aiming at solution of aforementioned problems, the inventors came to find magenta-forming couplers of 1H-pyrazolo[3,2-c]-s-triazole type which were excellent in both formaldehyd resistance, and light resistance of image, and high in color developability.

They are couplers of 1H-pyrazolo[3,2-c]-s-triazole type each of which is substituted by a tertiary alkyl group at the 3-position, and by another releasable group than a hydrogen atom at the 7-position, In other words, it was found that 1H-pyrazolo[3,2-c]-s-triazole compounds were made to largely improve in light resistance of image, and were given a high color developability by having been substituted by a tertiary alkyl group at the 3-position, and by another releasable group than a hydrogen atom at the 7-position.

As for said releasable group, the 7-position of a 1H-pyrazolo[3,2-c]-s-triazole compound is the position where said compound couples with the oxidation product of a color developing agent to form a magenta dye, and said releasable group at the 7-position is released through said coupling reaction Said 1H-pyrazolo[3,2-c]-s-triazole compound which is substituted by a tertiary alkyl group at the 3-position, and by another releasable group than a hydrogen group at the 7-position, is represented the following general formula:

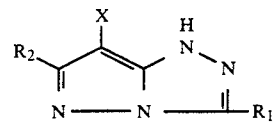

where $R_1$ is a tertiary alkyl group; $R_2$ is an alkyl, aryl or heterocyclic group. X is another releasable group than a hydrogen atom, which is released through coupling reaction of said compound with the oxidation product of a color developing agent.

The tertiary carbon atom of said tertiary alkyl group represented by $R_1$ is allowed to be substituted by, instead of an alkyl group, such an aryl group as a phenyl group; an alkoxy group an aryloxy group, an alkylthio group or the like. In addition, said tertiary carbon atom is allowed to participate also in the formation of another cyclic group. Furthermore, an alkyl group attached to said tertiary carbon atom is allowed to be substituted by a halogen atom; such an aryl group as a pheny group; a cyano group; a substituent group which links through a carbonyl group, such as an alkoxycarbonyl, acyl, or carbamoyl group; or a substituent group which links through a hetero atom, such as a nitro, alkoxy, alkylthio, arylthio, alkylsulfonyl, arylsulfonyl, alkylsulfinyl, arylsulfinyl, or dialkylamio group. Such a substituent group is especially preferably selected from among alkylthio, alkylsulfonyl, arylsulfonyl, alkylsulfinyl, and arylsulfinyl groups.

Further, needless to say, magenta-forming couplers in the invention include also bis-type 1H-pyrazolo[3,2-c]-s-triazole compounds, which are formed when the heterocyclic residue is a 1H-pyrazolo[3,2-c]-s-triazol-3-yl residue.

Such tertiary alkyl groups as above substantially include tert-butyl, 1,1-dimethyl-2-methoxyethyl, 1,1-dimethyl-2-cloroethyl, 1-methyl-1-phenylethyl, 1,1-di-n-amylhexyl, 7,7-dimethylnorbornan-1-yl, 1,1-dimethylbutyl, 1-ethyl-1-methylpropyl, and adamantyl groups.

The alkyl group represented by $R_2$ is allowed to be either primary, or secondary or tertiary, and to be substituted by a cyclic group, or any of the same substituent group as those for $R_1$ cited above.

The aryl group represented by $R_2$ is preferably a substituted or unsubstituted phenyl group. Substituent groups for said substituted group include alkyl, halogen, hydroxy, cyano, nitro, alkoxy, acylamino, sulfonamido, alkoxycarbonyl, carbamoyl, and carboxy group.

The heterocyclic group represented by $R_2$ is substantially a furyl, thienyl, or pyridyl group, or the like. Such a heterocyclic group is allowed to be substituted by any of the same substituent groups as those for the above aryl group as $R_2$.

The releasable group represented by X is allowed to be a halogen atom, or an organic group linked through an oxygen, nitrogen, or sulfur atom.

Among such releasable groups, those liked through an oxygen atom include alkoxy, aryloxy, acyloxy, and heterocyloxy groups. Those linked through an nitrogen atom include acylamino, diacylamino, and sulfonamido groups, and said-nitrogen-containing 5- or 6- membered heterocyclic groups. Those linked through an sulfur atom include thiocyano, alkylthio, arylthio, heterocyclothio, arylsulfonyl, and alkylsulfonyl groups.

Exemplary compounds embodied based on the invention are listed below, but the invention is not limited thereto:

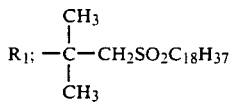 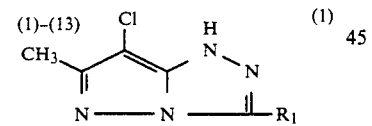 (1)

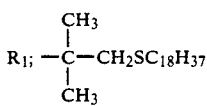 (2)

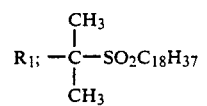 (3)

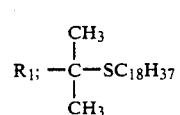 (4)

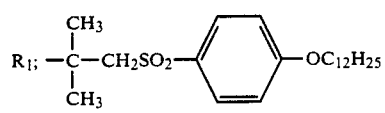 (5)

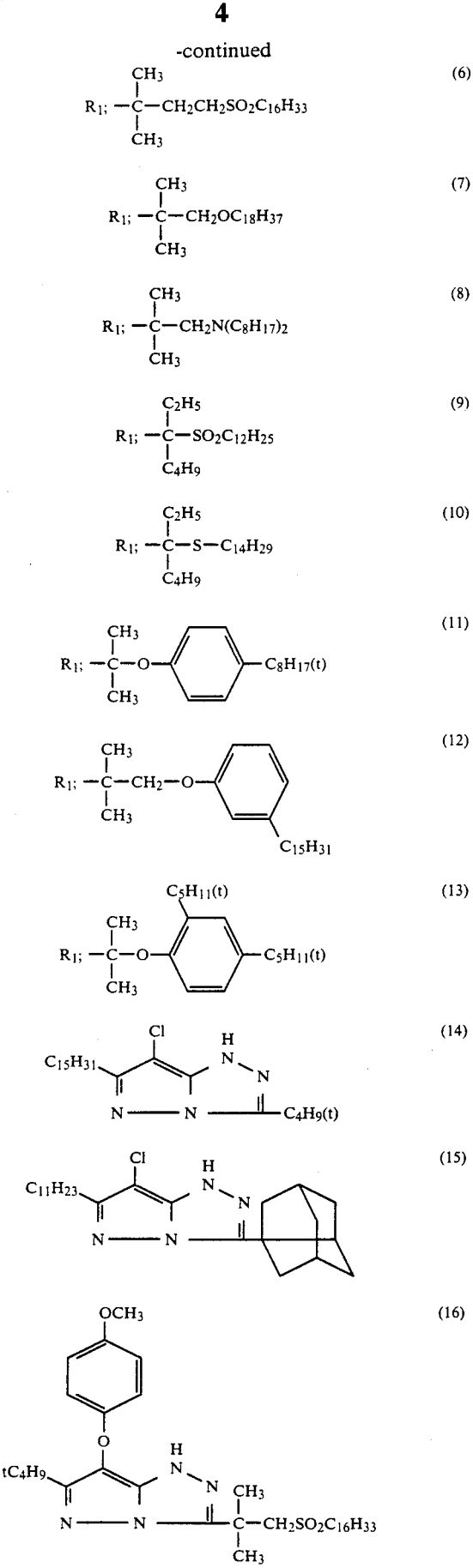

-continued

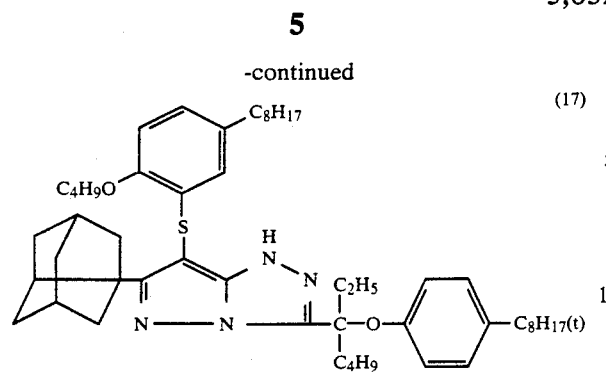 (17)

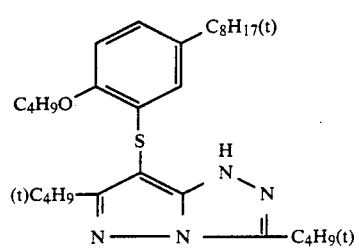 (18)

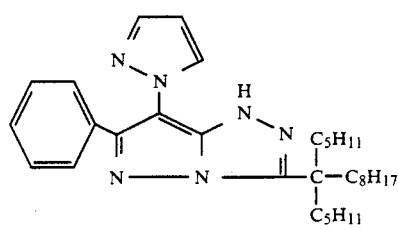 (19)

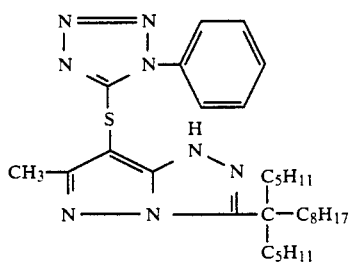 (20)

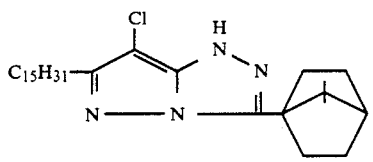 (21)

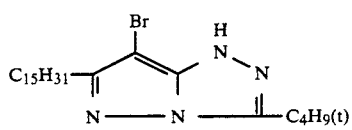 (22)

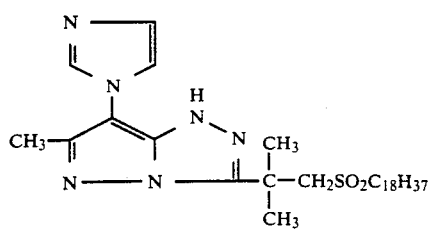 (23)

-continued

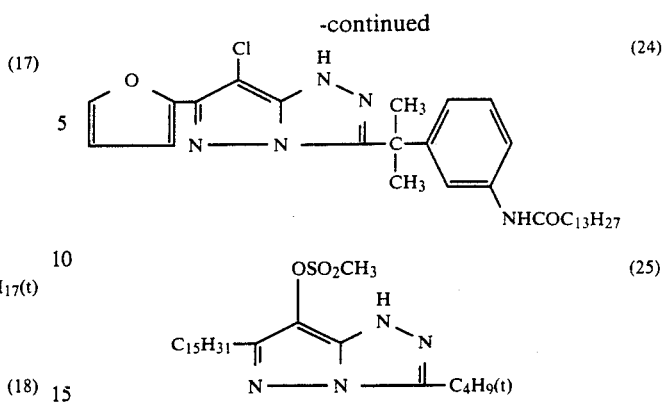

(24)

(25)

Description of typial synthetic processes of the above couplers of the invention is given below. The experimental synthesis was carried out on referring to the description in Research Disclosure, No. 12443; Journal of the Chemical Society I, 1977, P. 2047-2052; U.S. Pat. No. 3,725,067; and Japanese Patent C.P.I. Publication No. 99437/1984.

Synthesis of Compound (14)

The reaction scheme of the synthesis of Exemplary Compound (14) is represented as follows:

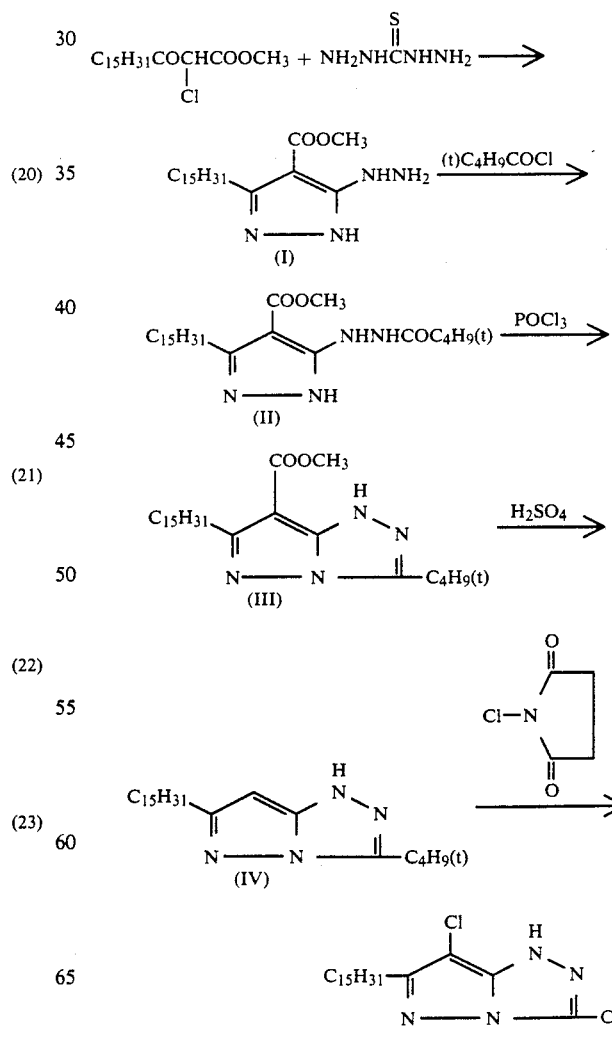

Compound (14)

Synthesis of (I)

First, 21.2 g of thiocarbohydrazide is added to 500 ml of ethanol, and refluxed. Then, 21.2 g of benzaldehyde is added dropwise to the solution, and refluxed for 1 hour. Further, 70 g of methyl α-chloro-α-palmitoylacetate is added to the solution, and refluxed for 5 hours. The resulting sulfur is filtered out, and the filtrate is added to with 30 g of hydrazine hydrate and is refluxed for 2 hours. On being cooled, the crude compound (I) is precipitated. The precipitate is filtered off, washed with water, and recrystallized from ethanol to obtain 31 g of the purified compound (I).

Synthesis of (II)

Both 27.5 g of (I) and 7.6 g of triethylamine are added to 200 ml of chloroform, and boiled under stirring. Then, 9.1 g of pivaloyl chloride is added dropwise to the solution, and refluxed for 1 hour. On being cooled, the resulting solution is washed with water, and dried with magnesium sulfate, and then chloroform is distilled away to precipitate crystals. Then, 27.6 g of the compound (II) is obtained by recrystallization of the crystals from acetone.

Synthesis of (III)

Both 27.0 g of (II) and 9.3 g of phosphorus exychloride are added to 200 ml of toluene, and refluxed for 4 hours. After removal of toluene by distillation under reduced pressure, the residue is added to with both 200 ml of acetonitrile and 12 g of pyridine, and refluxed for 1.5 hours. On being cooled, the resulting solution is poured into water to precipitate the crude compound (III). This is filterd out, washed with water, dried, and recrystallized from n-hexane to obtain 20.2 g of the pure compound (III).

Synthesis of (IV)

First, 18 g of (III) is added to a mixture of 100 ml of glacial acetic acid, 10 ml of concentrated sulfuric acid, and 5 ml of water, and refluxed flr 8 hours. After allowed to cool, the resulting solution is poured into ice water, and neutrallized with sodium hydroxide. The resulting precipitate is filtered off, washed well with water, dried, and recrystallized from acetonitrile to obtain 12.2 g of the compound (IV).

Synthesis of Exemplary Compound (14)

First, 11.2 g of (IV) us dissolved into 100 ml of chloroform. The solution is added to with 4.0 g of N-chlorosuccinimide, and is allowed to react together for 1 hour at room temperature. The resulting solution is washed with dilute alkali solution, and then washed with water well. After distilling away of chloroform, the residue is purified by column chromatography using silica gel carrier, and n-hexane/ethyl acetate (3:1) developing solvent. The product is recrystallized to obtain 6.8 g of Compound (14), and identified by nuclear magnetic resonance spectrometry, and mass spectrometry.

The silver halide color photo-sensitive material formed by the invention is allowed to contain a conventional dye-forming coupler in combination with that of the invention.

As a yellow-developing coupler among such conventional couplers, well-known compounds of open-chained type can be used, and compounds of benzoylacetanilide or pivaloylacetanilide type are especially useful. Such yellow-developing couplers include compounds described in U.S. Pat. Nos. 2,875,057, 3,265,506, 3,408,194, 3,551,155, 3,582,322, 3,725,072 and 3,891,445; West German Patent No. 1,547,868; West German OLS Patent Nos. 2,219,917, 2,261,361 and 2,414,006; British Patent No. 1,425,020; Japanese Patent Examined Publication No. 10783/1976; and Japanese Patent O.P.I. Publication Nos. 26133/1972, 73147/1973, 102636/1976, 6341/1975, 123342/ 1976, 130442/1975, 21827/1976, 87650/1975, 82424/1977 and 115219/1977.

As a useful cyan-developing coupler, there are cited phenol compounds, and naphthol compounds which include compounds described, for example, in U.S. Pat. Nos. 2,369,929 2,434,272, 2,474,293, 2,521,908, 2,895,826, 3,034,892, 3,311,476, 3,458,315, 3,476,563, 3,583,971, 3,591,383, 3,767,411 and 4,004,929; West German Patent Application (OLS) Nos. 2,414,830 and 2,454,329; Japanese Patent O.P.I. Publication Nos. 59838/1973, 26034/1976, 5055/1973, 146828/1976, 69624/1977 and 90932/1977.

As magenta-developing coupler, each of couplers of the invention is allowed to be used singly or in combination of two or more kinds. In addition, it is allowed to be used in combination with a well-known conventional coupler selected from among pyrazolone, indazolone, cyanoacetyl, pyrazolinobenzimidazole, and pyrazolotriazole compounds as the case may be.

Further, a certain colored coupler having a color correcting effect, or a certain coupler (DIR Coupler) releasing a development inhibitor, is allowed to be used in combination with a coupler of the invention if necessary.

The incorporation of a magenta-forming coupler of the invention, and of a certain coupler such as the above into a silver halide emulsion layer is conducted by well-known methods including the method described in U.S. Pat. No. 2,322,027.

Said couplers are dissolved into, for example, such a solvent as alkyl phthalate such as dibutyl phthalate, and dioctyl phthalate; phosphoric acid ester such as diphenyl phosphate, triphenyl phosphate, tricresyl phosphate, and dioctyl butyl phosphate; citric acid ester such as tributyl acetylcitrate; benzoic acid ester such as octyl benzoate; alkylamide such as diethyllauramide; aliphatic acid ester such as dibutoxyethyl succinate, and dioctyl acetate; trimesic acid ester such as tributyl trimesate; and such an organic solvent boiling at about 30° to 150° C. as ethyl acetate, butyl acetate, ethyl propionate, sec-butyl alcohol, methyl isobutyl ketone, β-ethoxyethyl acetate, and methyl cellosolve acetate, and then dispersed into a hydrophilic colloid. As a solvent, a mixture of a higher-boiling solvent and a lower-boiling solvent among the above also is allowed to be used.

In addition, the dispersing process with polymer, described in Japanese Patent Examined Publication No. 39853/ 1976, and Japanese Patent O.P.I. Publication No. 59943/1976, also can be used.

A magenta-forming coupler in the invention is added to a silver halide emulsion usually in the range of 0,005 to 2 moles per mole of silver halide, and preferably 0.03 to 0.5 moles per mole of silver halide.

While the dye image formed by a magenta-forming coupler of the invention generally exhibits a strong light-resistance by itself, the light resistance is further improved by means of the combined use of a certain antifading agent, or by the addition of a UV absorber-containing layer on the upper side.

As such an antifading agent, there are cited, for example, hydroquinone derivatives described in U.S. Pat. Nos. 2,360,290, 2,418,613, 2,675,314, 2,701,197, 2,704,713, 2,728,659, 2,732,300 2,735,765, 2,710,801 and 2,816,028, and British Patent No. 1,363,921; gallic acid derivatives described in U.S. Patent Nos. 3,457,079 and 3,069,262; p-alkoxyphenol compounds described in U.S. Patent Nos. 2,735,765 and 3,698,909, and Japanese Patent Examined Publication Nos. 20977/1974 and 6623/1977; p-oxyphenol derivatives described in U.S. Pat. Nos. 3,432,300, 3,573,050, 3,574,627 and 3,764,337, and Japanese Patent O.P.I. Publication Nos. 35633/1977, 147434/1977 and 152225/1977; and bisphenol compounds described in U.S. Pat. No. 3,700,455.

As the above UV absorber, there are cited, for example, aryl-substituted benzotriazole compounds described, for example, in U.S. Pat. No. 3,533,794; 4-thiazolidone compounds des cribed, for example, in U.S. Pat. Nos. 3,314,794 and 3,352,681; benzophenone compounds described, for example, in Japanese Patent O.P.I. Publication No. 2784/1971; cinnamic acid ester compounds described, for example, un U.S. Pat. Nos. 3,705,805 and 3,707,375; butadiene compounds described, for example, in U.S. Pat. No. 4,045,229; benzoxidole compounds described, for example, in U.S. Pat. No. 3,700,455; and compounds described in U.S. Pat. No. 3,499,762, and Japanese Patent O.P.I. Publication No. 48535/1979.

As silver halide used in the silver halide emulsion in the invention, there are cited those used commonly silver halide emulsion in the art, such as silver bromide, silver chloride, silver iodobromide, silver chlorobromide, and silver chloroiodobromide.

Silver halide used in the invention is spectrosensitized by an appropriately selected sensitizing dye so as to be provided with the cdlor sensitivity to the light of the required range of wavelength. Said sensitizing dyes include cyanine dyes, merocyanine dyes, composite cyanine dyes, composite merocyanile dyes, holopolar cyanie dyes, hemicyanine dyes, styryl dyes, and hemioxonole dyes.

As an especially useful sensitizing dye, there are cited those described, for example, in West German Patent No. 929,080; U.S. Pat. Nos. 2,231,658, 2,493,748, 2,503,776, 2,519,001, 2,912,329, 3,656,959, 3,672,897, 3,694,217, 4,025,349 and 4,046 572; British Patent No. 1,242,588; and Japanese Patent Examined Publication Nos. 14030/1969 and 24844/1977.

While these sensitizing dyes are allowed to be either singly or in combination one another, they are often used in combination for the purpose of intensive sensitization, as typically shown, for example, in U.S. Pat. Nos. 2,688,545, 2,977,229, 3,897,060, 3,522,052, 3,527,641, 3,617,293, 3,628,964, 3,666,480, 3,672,898, 3,679,428, 3,703,377, 3,769,301, 3,814,609, 3,837,862 and 4,026,707; British Patent Nos. 1,344,281 and 1,507,803; Japanese Patent Examined Publication Nos. 4936/1968 and 12375/1978; and Japanese Patent O.P.I. Publication Nos. 110618/1977 and 109925/1977.

Silver halide emulsions used in the invention can contain various well-known photographic additives described, for example, in Research Disclosure, No. 17643.

The support of the silver halide color photo-sensitive material of the invention can be selected from among well-known materials including plastic film, plastic-laminated paper, baryta paper, and synthetic paper, according to the purpose.

Thus constituted silver halide color photo-sensitive material of the invention can be submitted to various color developing processings after exposure.

Color developing agents of aromatic primary amine type used in color developers in the invention include well-known compounds being widely used in various color photographic processings. These developing agents include both aminophenol derivatives, and p-phenylenediamine derivatives. In general, these compounds are used in the form of salt such as hydro chloride and sulfate rather than in the form of free amine, because of more stable nature of the salt. They are usually used at concentrations from about 0.1 to about 30 grams, and preferably from about 1 to about 1.5 grams per liter of developer.

Said developing agents of aminophenol type include o-aminophenol, p-aminophenol 5-amino-2-hydroxytoluene, 2-amino-3-hydroxytoluene, and 2-hydroxy-3-amino-1,4-dimethylbenzene, for example. Especially useful color developing agents of aromatic primary amine type are N,N'-dialkyl-p-phenylenediamine compounds, whose alkyl groups and/or phenylene group is allowed to have arbitrary substituent groups. Thus, especially useful compounds, substantially are N,N'-diethyl-p-phenylenediamine hydrochloride, N-methyl-p-phenylenediamine hydrochloride, N,N'-dimethyl-p-phenylenediamine hydrochloride, 2-amine-5-(N-ethyl-N-dodecylamino) toluene, N-ethyl-N-$\beta$-methanesulfonamidoethyl-s-methyl-4-aminoaniline Sulfate, N-ethyl-N-$\beta$-hydroxyethylaminoaniline, 4-amino-3-methyl-N,N'-diethylaniline, and 4-amino-4-(2-methoxyethyl)-N-ethyl-3-methylaniline p-toluenesulfonate, for example.

A color developer used in processing in the invention is allowed to arbitravily contain, besides the anove color developing agent of aromatic primary amine type, such various additives, which are commonly added to color developers, as sodium hydroxide, sodium carbonate, and other alkaline agents; alkali metal sulfites, alkali metal bisulfites, alkali metal thiocyanates, alkali metal halides, benzyl alcohol, water-softening agents, and thickening agents. The pH of the color developer for the invention is usually more than 7.0, and very often about 10 to 13.

After color development, the silver halide photo-sensitive material of the invention is treated with by a processing solution capable of fixing the color. When said processing solution is a fixer, said material is preliminarily submitted to a bleaching treatment. A metal complex of organic acid is used as a bleaching agent in the bleaching solution or bleach-fix solution used in said bleaching process. Such a metal complex is capable of oxidizing metallic silver formed through developing process, to silver halide, and of color-developing undeveloped part of the color developing agent at the same time. Said metal complex is formed by coordinating such a metal as iron, cobalt, and copper to such an organic acid as aminopolycarboxylic acid, oxalic acid, and citric acid. Such an organic acid is especially preferably a polycarboxylic acid, or aminopolycarboxylic acid. Said polycarboxylic acid, or aminopolycarboxylic acid is useful also in the form of its alkali metal or ammonium salt, or water-soluble amine salt.

Thus organic acids, and their salts useful to form said metal complexes include the following typical compounds:
(1) Ethylenediaminetetraacetic acid
(2) Diethylenetriaminepentaacetic acid (3) Ethylenediamine-N-(β-hydroxyethyl)-N',N',N'triacetic acid
(4) Propylenediaminetetraacetic acid
(5) Nitrilotriacetic acid
(6) Cyclohexanediaminetetraacetic acid
(7) Iminodiacetic acid
(8) Dihydroxyethylglycinecitric acid (or -succinic acid)
(9) Ethyletherdiaminetetraacetic acid
(b 10) Glycoletherdiaminetetraacetic acid
(11) Ethylenediaminetetrapropionic acid
(12) Phenylenediaminetetraacetic acid
(13) Disodium ethylenediaminetetraacetate
(14) Tetratrimethylammonium ethylenediaminetetraacetate
(15) Tetrasodium ethylenediaminetetraacetate
(16) Pentasodium diethylenetriaminepentaacetate
(17) Sodium ethylenediamine-N-[β-hydroxyethyl)-N,N', N'-triacetate
(18) Sodium propylenediaminetetraacetate
(19) Sodium nitrilotriacetate
(20) Sodium cyclohexanediaminetetraacetate The bleaching solution used in said processing can contain various additives besides the above organic acid salts. Such additives are especially desirable to include alkali or ammonium halides as rehalogenation agent such as potassium bromide, sodium bromide, sodium chloride, and ammonium bromide; metal salts; and sequestering agents. The bleaching solution can contain also various other additives well-known as common bleaching solution additives, such as borates, oxalates, acetates, carbonates and phosphates as a pH buffer agent; alkylamines; polyethylene oxide compounds, as the case may be.

Further, said fixer or bleach-fix solution is allowed to contain, either singly or in combination of two or more kinds, pH buffer which is composed of such sulfites as ammonium sulfite, potassium sulfite, ammonium bisulfite, potassium bisulfite, sodium bisulfite ammonium metabisulfite, potassium metabisulfite and sodium metabisulfite; boric acid, boxax, sodium hydroxide; such salts as sodium carbonate, potassium carbonate, sodium bicarbonate, potassium bicarbonate, sodium acetate; acetic acid, and ammonium hydroxide.

When the bleach-fix processing is conducted while more bleach-fix solution is supplemented the bleach-fix bath, such salts as thiosulfates, thiocyanates, and bisulfates are allowed to be contained by either said bleach-fix bath, or said supplementary bleach-fix solution.

In the invention, it is allowed, for the purpose of improving the activity of the bleach-fix solution, that air or oxygen is blown into either bath or storage vessel of the solution, or that a certain pertinent oxidizing agent such as hydrogen peroxide, bromate, and persulfate is added, as the case may be.

(EXAMPLE)

Further description of the invention is made as follows, giving examples, but the invention is not limited to these examples.

EXAMPLE 1

Each of both magenta-forming couplers of the invention, and couplers for reference as listed in Table 1, was separately taken by an amount of 0.1 mole per mole of Ag, and throughly dissolved into the mixture of the same amount of tricresyl phosphate, and three-fold amount of ethyl acetate by heating at 60° C. The solution was mixed with 1200 ml of 5% gelatin aqueous solution which contained 120 ml of 5% Alkanol B (alkyl naphthalenesulfonate; E.I. du Pont) aqueous solution, and emulsified by an ultrasonic dispersing device. Then, the emulsified product was added to 4 kg of a green-sensitive silver iodobromide emulsion (containing 6 mole % of silver iodide), and was joined by 120 ml of 2% 1,2-bis(vinyl-sulfonyl)ethane (as a hardener) methanolic aqueous (1:1) solution. The obtained emulsion was applied on an undercoated transparent polyester base at a rate of 20 mg of applied Ag per 100 $cm^2$ of base, to make the sample.

The obtained sample was exposed through an optical wedge according to the usual way, and then submitted to the development processing. Results are shown in Table 1.

| (Developing process) | | |
|---|---|---|
| Color developing | 38° C. | 3¼ minutes |
| Bleaching | 38° C. | 4½ minutes |
| Washing | 38° C. | 3¼ minutes |
| Fixing | 38° C. | 4½ minutes |
| Washing | 38° C. | 3¼ minutes |
| Stabilizing | 38° C. | 1½ minutes |
| Drying | 47° C. ± 5° C. | 16½ minutes |
| (Color developer) | | |
| Potassium carbonate | | 30.0 g |
| Sodium hydrogen carbonate | | 2.5 g |
| Potassium sulfite | | 5.0 g |
| Sodium bromide | | 1.3 g |
| Potassium iodide | | 2 mg |
| Hydroxylamine sulfate | | 2.5 g |
| Sodium chloride | | 0.6 g |
| Sodium diethylenetriamine-pentaacetate | | 2.5 g |
| 4-Amino-3-methyl-N-ethyl-N-(β-hydroxyethyl)aniline sulfate | | 4.8 g |
| Potassium hydroxide | | 1.2 g |
| Water to make | | 1000 ml |
| Potassium hydroxide or 20% surfuric acid to make | pH | 10.06 |
| (Bleaching Solution) | | |
| Ferric ammonium ethylenediaminetetraacetate | | 100 g |
| Ethylendiaminetetraacetic acid | | 10 g |
| Ammonium bromide | | 150 g |
| Glacial acetic acid | | 40 ml |
| Sodium bromate | | 10 g |
| Water to make | | 1000 ml |
| Aqua ammonia or glacial acetic acid to make | pH | 3.5 |
| (Fixer) | | |
| Ammonium thiosulfate | | 180 g |
| Sodium sulfite, anhydrous | | 12 g |
| Sodium metabisulfite | | 2.5 g |
| Disodium ethylenediaminetetraacetate | | 0.5 g |
| Sodium carbonate | | 10 g |
| Water to make | | 1000 ml |
| (Stabilizer) | | |
| Formalin, 37% | | 2 ml |
| Konidaks (Konishiroku) | | 5 ml |
| Water to make | | 1000 ml |

TABLE 1

| No. | Coupler | Spec. Sens.[1] | Max. Dens. | $CH_2O$ resist[2] | Light resist.[3] |
|---|---|---|---|---|---|
| 11 | Ref. 1 | 100 | 2.65 | 92 | 25 |
| 12 | Ref. 2 | 44 | 1.30 | 48 | 23 |
| 13 | Inv.(14) | 100 | 2.59 | 95 | 32 |
| 14 | Inv.(22) | 102 | 2.69 | 92 | 31 |
| 15 | Inv.(25) | 105 | 2.78 | 91 | 34 |

Notes:
[1] The specific sensitivity was represented as reciprocal of the exposure quantity which gave a density of (fog density ± 0,1), based on 100 for Sample No. 11.
[2] The formal dehyde ($CH_2O$) resistance was determined in the following way:

TABLE 1-continued

Preliminarily, 0.9% formaldehyde aqueous solution is prepared, and conditioned to 30° C. and 6% RH. Six(6) ml of the solution is placed in a closed vessel. The sample is placed in the vessel for 3 days, and then is color-developed. A reference sample untreated with formaldehyde also is color-developed concurrently.

Formaldehyde resistance = $\frac{\text{Color density of Sample}}{\text{Color density of Ref.}} \times 100(\%)$ (3) The light resistance was determined in the following way:
The color developed sample is irradiated for 5 days by a xenon fade meter. The percent residual dye is determined based on 1.0 for the initial density.

Light resistance = $\frac{\text{Density after irrad.}}{1.0} \times 100(\%)$

Reference Coupler 1

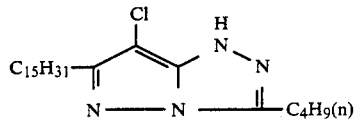

Reference Coupler 2

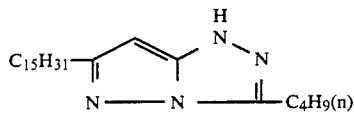

It proves clear from Table 1 that couplers of the invention are improved in color developability, formaldehyde resistance, and light resistance in comparison with reference couplers.

EXAMPLE 2

Each of Samples 11 to 15 of Example 1 are exposed through an optical wedge in the same way as in Example 1, and developed and processed under the conditions cited below. Results are shown in Table 2. The specific sensitivity and the light resistance were determined in the same way as in Example 1.

| (Developing process) | | | |
| --- | --- | --- | --- |
| Color developing | 38° C. | 3½ | minutes |
| Bleaching-fixing | 38° C. | 1½ | minutes |
| Stabilizing and/or washing | 25 to 30° C. | 3 | minutes |
| Drying | 75 to 80° C. | about 2 | minutes |
| (Color developer) | | | |
| Benzyl alcohol | | | 15 ml |
| Ethylene glycol | | | 15 ml |
| Potassium sulfite | | | 2.0 g |
| Potassium bromide | | | 0.7 g |
| Sodium chloride | | | 0.2 g |
| Potassium carbonate | | | 30.0 g |
| Hydroxylamine sulfate | | | 3.0 g |
| Polyphosphoric acid (TPPS) | | | 2.5 g |
| 3-Methyl-4-amino-N-ethyl-N-(β-methanesulfonamidoethyl) aniline sulfate | | | 5.5 g |
| OBA (4,4-Diaminostilbenedisulfonic acid derivative) | | | 1.0 g |
| Potassium hydroxide | | | 2.0 g |
| Water to make | | | 1000 ml |
| Make | | pH | 10.20 |
| (Bleach-fix-solution) | | | |
| Ferri ammonium ethylenediamine tetraacetate dihydrate | | | 60 g |
| Ethylenediaminetetraacetic acid | | | 3 g |
| Ammonium thiosulfate, 70% soln. | | | 100 ml |
| Ammonium sulfite, 40% soln. | | | 27.5 ml |
| Potassium carbonate or glacial acetic acid to make | | pH | 7.1 |
| Water to make | | | 1000 ml |
| (Stabilizer) | | | |
| 5-Chloro-2-methyl-4-isothiazolin-3-on | | | 1.0 g |
| Ethylene glycol | | | 10 g |

TABLE 2

| No. | Coupler | Spec. sens. | Max. dens. | Light resist. |
| --- | --- | --- | --- | --- |
| 2-21 | Ref. 1 | 100 | 2.42 | 23 |
| 2-22 | Ref. 2 | 49 | 1.30 | 22 |
| 2-23 | Inv. (14) | 103 | 2.42 | 33 |
| 2-24 | Inv. (22) | 99 | 2.39 | 35 |
| 2-25 | Inv. (25) | 101 | 2.45 | 35 |

EXAMPLE 3

A silver halide color photo-sensitive material was prepared by applying the following layers (1) to (6) in this order on a support paper which had been coated with polyethylene resin containing anatase-form titanium dioxide. All the doses of additives are represented as weight in mg per 100 cm² of support.

(1) A layer which contains 20 mg of gelatin, a blue-sensitive silver chlorobromide emulsion containing 5 mg of Ag and 8 mg of a Y-coupler plus 0.1 mg of 2,5-di-tert-octylhydroquinone which has been dissolved in 3 mg of dioctyl phthalate.

(2) A UV absorber-containing intermediate layer which contains 12 g of gelatin, and 0.5 mg of 2,5-di-tert-octylhydroquinone plus 4 mg of a UV absorber which has been dissolved in 2 mg of dibutyl phthalate.

(3) A layer which contains 18 mg of gelatin, a green-sensitive silver chlorobromide emulsion containing 4 mg of Ag, and 5 mg of an M-coupler plus 2 mg of an antioxidant plus 0.2 mg of 2,5-di-tert-octylhydroquinone which has been dissolved in 2,5 mg of dioctyl phthalate.

(4) An intermediate layer which contains the same additives as in the layer (2).

(5) A layer which contains 16 mg of gelatin, a red-sensitive silver chlorobromide emulsion containing 4 mg of As, and 3,5 mg of a C-coupler plus 0,1 mg of 2,5-di-tert-octylhydroquinone which has been dissolved in 2,0 mg of tricresyl phosphate.

(6) A protective gelatin layer which contains 9 mg of gelatin.

Each of layers (1) to (6) was added to with a certain coating aid, and each of layers (4) and (6) was added to also with a certain gelatin cross-linking agent.

As a UV absorber for layers (2) and (4), a certain mixture of compounds (UV-1 and UV-2 illustrated layer.

As an autioxidant for the layer (3), di-tert-pentylhydroquinone dioctyl ether.

The above multilayered photo-sensitive material was processed in the same way as in Example 2. Obtained results are shown in Table 3 with the kind of used Y-, M-, and C-couplers.

Each sample was evaluated as to its magenta density after exposure to the white light. The specific sensitivity and the light resistance were determined in the same way as in Example 1.

It proves clear from Table 3 that couplers of the invention are improved in light resistance of their dye image, and that said light resistance is further improved by the combined use of a certain UV absorber. UV absorbers:

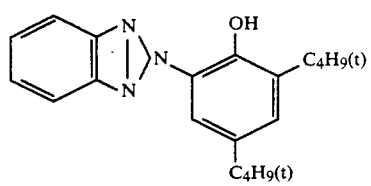
UV-1
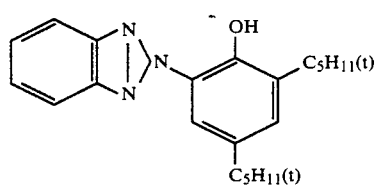
UV-2
Y-Couplers:
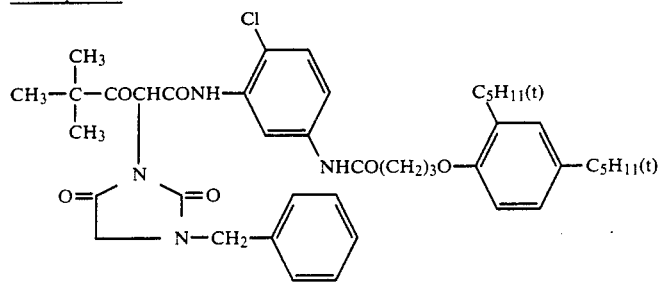
Y-1
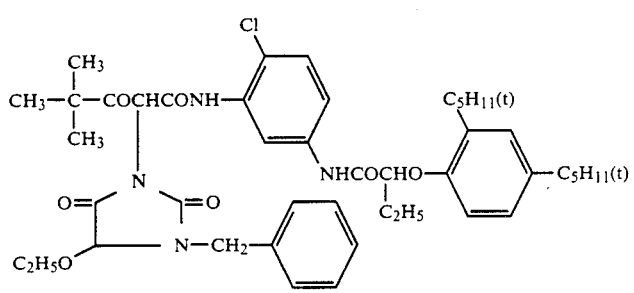
Y-2
C-Couplers:
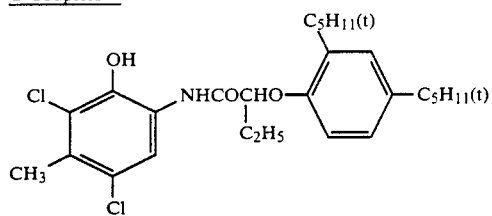
C-1
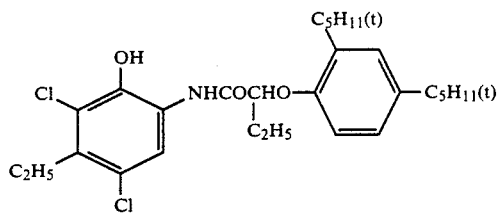
C-2
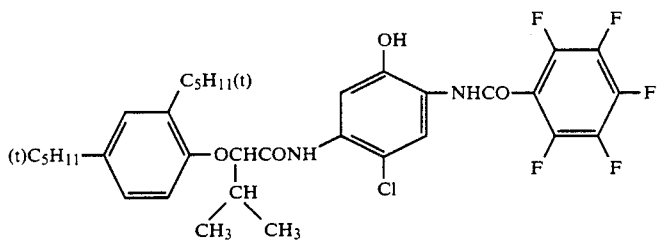
C-3

-continued

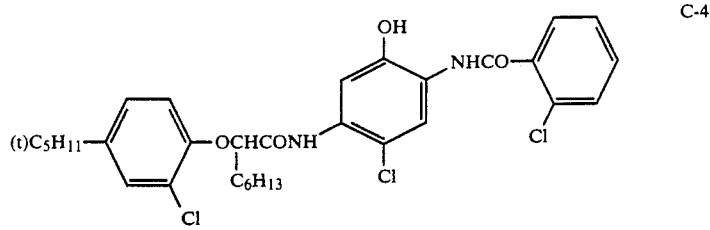

C-4

TABLE 3

| No. | Layer (1) Y-Coupler | Layer (3) M-Coupler | Layer (5) C-Coupler | Layer (5) UV absorber | Spec. sens. | Max. dens. | Light resist. | Note |
| --- | --- | --- | --- | --- | --- | --- | --- | --- |
| 31 | Y-1 | Ref. (1) | C-1 | — | 100 | 2.31 | 23 | |
| 32 | Y-1 | Ref. (1) | C-1 | UV-1,-2 | 102 | 2.30 | 30 | Further added 2 mg UV absorber to Layer (5) |
| 33 | Y-1 | Inv. (14) | C-1 | — | 99 | 2.29 | 35 | |
| 34 | Y-1 | Inv. (14) | C-1 | UV-1,-2 | 103 | 2.33 | 40 | |
| 35 | Y-2 | Inv. (14) | C-2 | UV-1,-2 | 98 | 2.26 | 41 | |
| 36 | Y-2 | Inv. (14) | C-2 | UV-1,-2 | 99 | 2.28 | 46 | Applied layer same as Layer (2) between Layers (5) & (6) of No. 35. |
| 37 | Y-1 | Inv. (14) | C-3 | UV-1,-2 | 105 | 2.38 | 39 | |
| 38 | Y-1 | Inv. (14) | C-3 | UV-1,-2 | 103 | 2.35 | 45 | Same layer structure as No. 37. |
| 39 | Y-2 | Inv. (14) | C-4 | UV-1,-2 | 97 | 2.29 | 42 | |
| 40 | Y-2 | Inv. (14) | C-1 | UV-1,-2 | 101 | 2.30 | 41 | |
| 41 | Y-1 | Inv. (25) | C-1 | UV-1,-2 | 103 | 2.36 | 41 | |

What is claimed is:

1. A silver halide photosensitive material having at least one silver halide emulsion layer on a support, said silver halide emulsion layer containing at least one magenta-forming coupler of the 1H-pyrazolo(3,2-c)-s-triazole type which is substituted by a tertiary alkyl group at the 3-position, by a primary alkyl group, a secondary alkyl group, an aryl group, or a heterocyclic ring group at the 6-position; and by a releasable group other than a hydrogen atom at the 7-position, said tertiary alkyl group at the 3-position having a carbon atom directly coupled to the 1H-pyrazolo(3,2-c)-s-triazole nucleus, said carbon atom having no hydrogen atom attached thereto.

2. The silver halide color photo-sensitive material as claimed in claim 1, wherein said magenta-forming coupler of 1H-pyrazolo[3,2-c]-S-triazole type is a compound represented by the following formula;

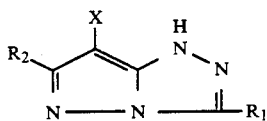

wherein $R_1$ represents a tertiary alkyl group; $R_2$ represents an primary alkyl group, secondary alkyl group an aryl group or a heterocyclic ring group; and X represents a split-off group other than hydrogen, which is capable of splitting off through a coupling reaction with the oxidation products of an aromatic amine color developing agent.

3. The silver halide color photo-sensitive material as claimed in claim 1, wherein said silver halide emulsion layers are those spectrally sensitized in blue, green and red, respectively, and the green-sensitive layer contains said magenta-forming coupler of 1H-pyrazolo3,2-c]-S-triazole type in an amount of from 0.005 mole to 2 mole per mole of the silver halide used.

4. The silver halide color photo-sensitive material as claimed in claim 3, wherein said green-sensitive layer contains said magenta-forming coupler of 1H-pyrazolo[3,2-c-S-triazole type in an amount of from 0.03 mole to 0.5 mole per mole of the silver halide used.

5. The silver halide color photo-sensitive material as claimed in claim 3, wherein said blue-sensitive layer contains at least one yellow-forming coupler selected from the group consisting of those of benzoylacetanilide type and of pivaloylacetanilide type.

6. The silver halide color photo-sensitive material as claimed in claim 3, wherein said red-sensitive layer contains at least one cyan-forming coupler selected from the group consisting of those of phenol type and of naphthol type.

7. The silver halide color photo-sensitive material as claimed in claim 3 , wherein said blue-sensitive layer contains at least one of the yellow-forming couplers claimed in claim 5, and said red-sensitive layer contains at least one of the cyan-forming couplers claimed in claim 6.

8. The silver halide color photo-sensitive material as claimed in claim 2, wherein X represents a halogen atom.

9. The silver halide color photo-sensitive material as claimed in claim 2, said tertiary alkyl group represented by $R_1$ has 4 to 25 carbon atoms.

10. The silver halide color photo-sensitive material as claimed in claim 2, said primary alkyl group represented by $R_2$ has 1 to 15 carbon atoms.

* * * * *

UNITED STATES PATENT AND TRADEMARK OFFICE
CERTIFICATE OF CORRECTION

PATENT NO. : 5,032,497
DATED : July 16, 1991
INVENTOR(S) : Noritaka Nakayama et al.

It is certified that error appears in the above-indentified patent and that said Letters Patent is hereby corrected as shown below:

Claim 2, column 17, line 45, change "-S-" to -- -s- --.
Col. 17, line 55, after, "group" (second occurrence
insert --,--.

Claim 2, column 17, line 58, change "ofs plitting"
to --of splitting--.

Claim 3, column 18, line 31, change "1H-pyrazolo3,2-c]-S-"
to --1H-pyrazolo[3,2-c]-s- --.

Claim 4, column 18, line 37, change
"pyrazolo[3,2-c-S-triazole" to
--pyrazolo[3,2-c]-s-triazole--.

Signed and Sealed this

Twenty-fourth Day of August, 1993

Attest:

BRUCE LEHMAN

*Attesting Officer*   *Commissioner of Patents and Trademarks*